(12) United States Patent
Silley et al.

(10) Patent No.: US 6,265,210 B1
(45) Date of Patent: Jul. 24, 2001

(54) CONTROLLED ATMOSPHERE EQUIPMENT

(75) Inventors: Peter Silley, Bingley; Michael John Annable, Silsden, both of (GB)

(73) Assignee: Don Whitley Scientific Limited, Shipley (GB)

( * ) Notice: Subject to any disclaimer, the term of this patent is extended or adjusted under 35 U.S.C. 154(b) by 0 days.

(21) Appl. No.: 09/254,754
(22) PCT Filed: Sep. 8, 1997
(86) PCT No.: PCT/GB97/02411
 § 371 Date: Mar. 8, 1999
 § 102(e) Date: Mar. 8, 1999
(87) PCT Pub. No.: WO98/10054
 PCT Pub. Date: Mar. 12, 1998

(30) Foreign Application Priority Data

Sep. 9, 1996 (GB) .................................................. 9618785
Apr. 26, 1997 (GB) .................................................. 9708431

(51) Int. Cl.$^7$ .................................................. C12M 1/00
(52) U.S. Cl. .................................. 435/303.1; 435/303.2; 435/3; 435/286.6; 435/801; 435/809; 600/22; 422/104
(58) Field of Search ................ 435/303.1, 303.2, 435/303.3, 286.6, 809, 801, 3, 41, 325, 243; 600/21, 22; 422/104; 119/311

(56) References Cited

U.S. PATENT DOCUMENTS 4,336,329 * 6/1982 Hesse et al. .............................. 435/3

FOREIGN PATENT DOCUMENTS 0 411 794 A1 * 2/1991 (EP) .
WO 96/11092 * 4/1996 (WO) .

* cited by examiner

Primary Examiner—David A. Redding
(74) Attorney, Agent, or Firm—Chapman and Cutler

(57) ABSTRACT

Controlled atmosphere cabinet has enclosure (110;210) with means providing visibility (110F; 210F) of its interior from outside, gas supply (113–116, 212–216) for desired or target composition of internal atmosphere, controlled lock-type access (112) for manual introduction and removal of items, and hand/arm access port provision (111A, B; 211A, B) for manipulation of said samples in the cabinet. Gas supply associated control means (230–240) serves during use of the cabinet (other than normal atmosphere augmenting in use of the lock-type access) for additional gas supply further to correct or compensate for effects actually or potentially adverse to maintaining the desired or target internal atmosphere composition, via operator-actuated input means (121t, 123; 222) and/or means (122, 124, 139; 225) for sensing prescribed conditions to which the control means is responsive for said additional gas supply.

14 Claims, 5 Drawing Sheets

CONTROLLED ATMOSPHERE EQUIPMENT

DESCRIPTION

Figure 1:
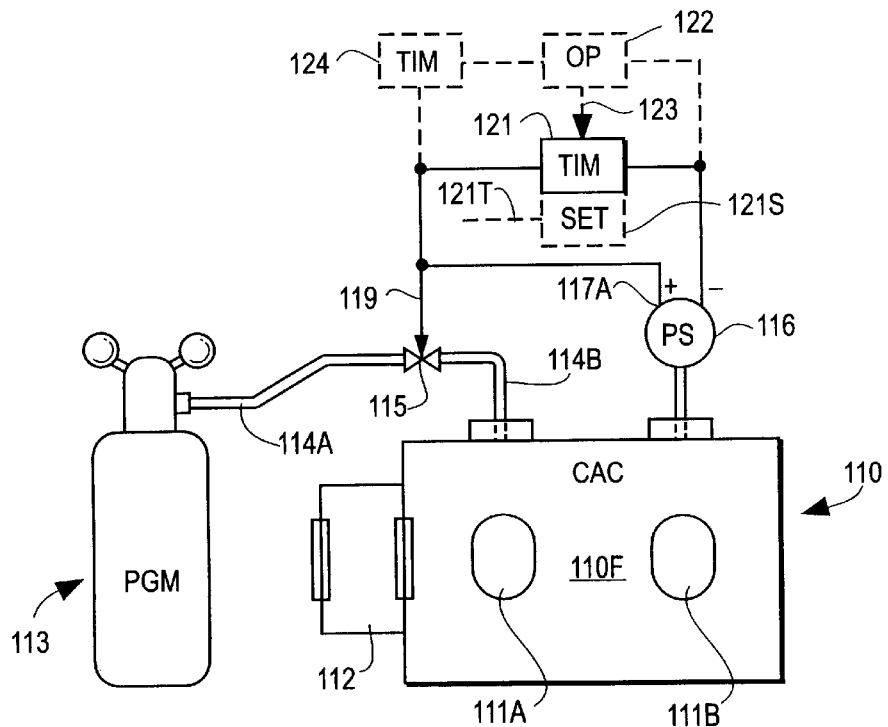

This invention relates to controlled atmosphere equipment, such as, but not limited to cabinets useful in microbiology laboratories for maintaining a prescribed or prescribable atmosphere, not necessarily anaerobic.

Typical so-called variable atmosphere microbiological nurture cabinets are known, including as we have previously supplied commercially, with provision for an operator to set a desired internal atmosphere composition, typically relative to content levels of hydrogen and/or carbon dioxide and/or oxygen and/or nitrogen. Such desired composition can be set by flow rates of constituent gases, typically from cylinders as compressed supplies thereof.

Aspects of this invention arise by way of seeking to improve actual internal cabinet atmosphere in terms of better maintaining or departing less from a desired or specified target for the atmosphere actually within the cabinet, effectively to compensate or correct for actually or potentially adverse relevant effects, say from greater/other than normal use including as to loading and unloading the cabinet, or due to the microbiological activity taking place within the cabinet having differential effects on component gases of target atmosphere.

In a first incentive aspect, a specified gas mixture for supply purposes in setting up some target internal atmosphere is subsequently further supplied after such setting up not only so as to maintain any desired internal normally slightly positive atmospheric pressure, say as demanded by reference to a pressure switch or transducer, but also on a regular basis- which may be adjustable, whether by operator selection or in response to sensed conditions, say effectively as a prescribable circulation involving both gas-supply and removal or venting.

Such circulation can, with advantages be done by injection of more gas before removal or venting, i.e. increasing normal overpressure, say until sensed by a suitable device then automatically causing opening of gas removal or venting valve provision, whether simply relative to achieving such overpressure or for a further prescribed time of gas supply and/or relative to reducing to a lower, say normal, overpressure at least after such prescribed further times of further gas supply.

It is found to be particularly convenient for at least such prescribable regular further gas supply to be accompanied by positive removal of any accumulated condensate, say preferably using a peristaltic pump which can also contribute to or assist in cabinet atmosphere removal, at least after condensate removal is complete.

Beneficial effect can be simply to increase tendency towards maintaining a prescribed or target atmosphere, say as represented by flow rates of constituent gas. Further beneficial effect can be gained by taking account of such effects of particular microbiological action(s) of current interest as may be known or determined by further investigation in terms of differential effects on component gases, say than by further prescribed modification of supplied gas mixture, as further supplied, say increasing flow rate(s) of one more and/or reducing other(s), i.e. compared to normal target mix flows, god according to type of such action(s) or further as to number(s) of samples involved.

Yet closer internal atmosphere control can be obtained by sensing particular content(s) of one or more or all of constituent gases and computing individual gas flow rates to compensate, whether wholly or partly.

Figure 2:
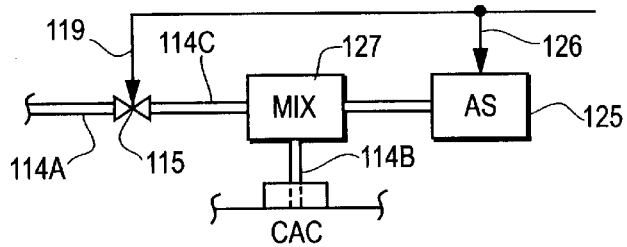
Figure 4:
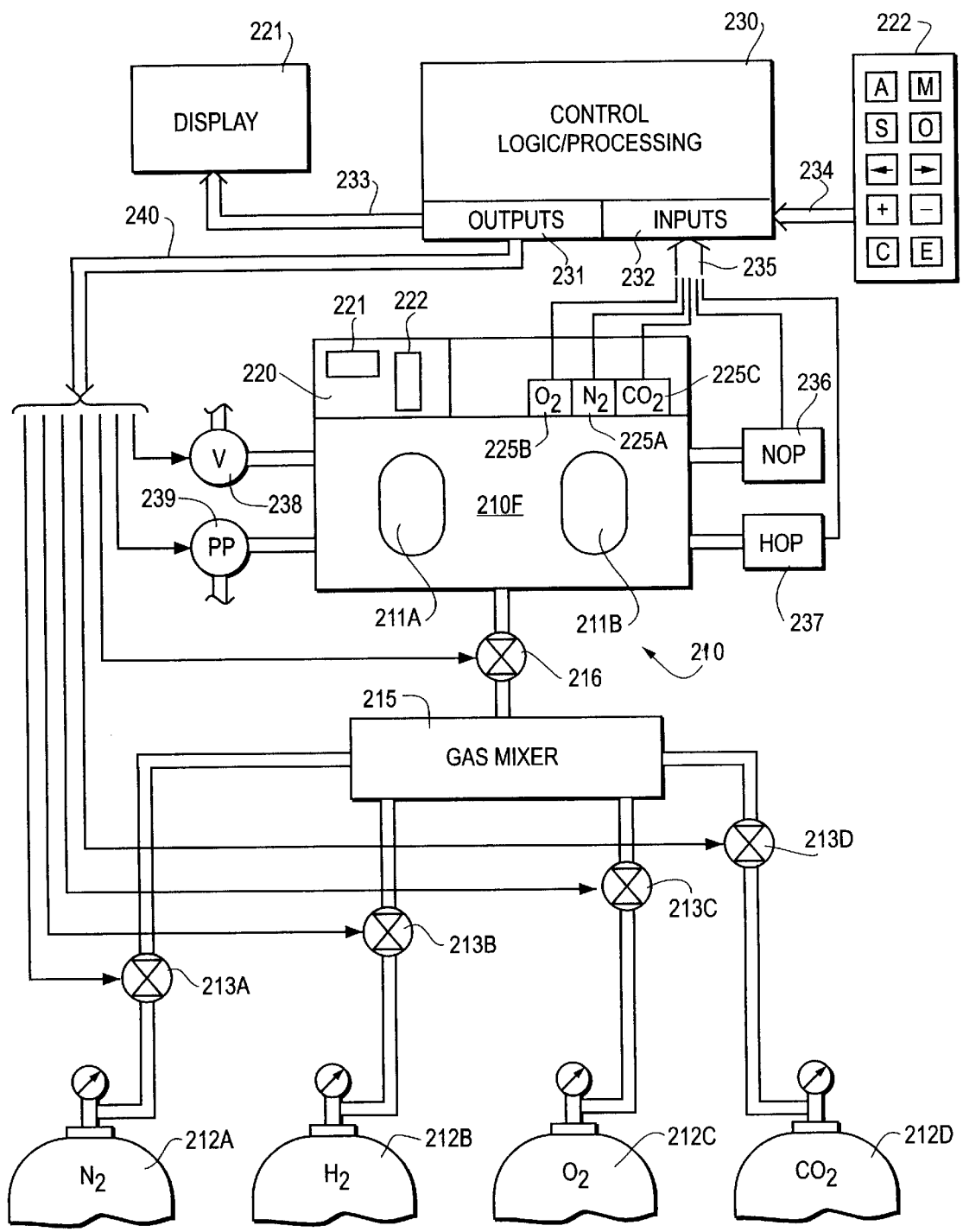

Specific implementations in practical embodiments of this invention will now be indicated and described, by way of example, with reference to the accompanying diagrammatic drawings, in which FIG. 1 is an outline atmospheric gas flow control provision for a first embodiment;

FIGS. 2. and 3 are modifications or alternatives;

FIG. 4 is an outline atmosphere control provision for another embodiment; and

Figure 5A:
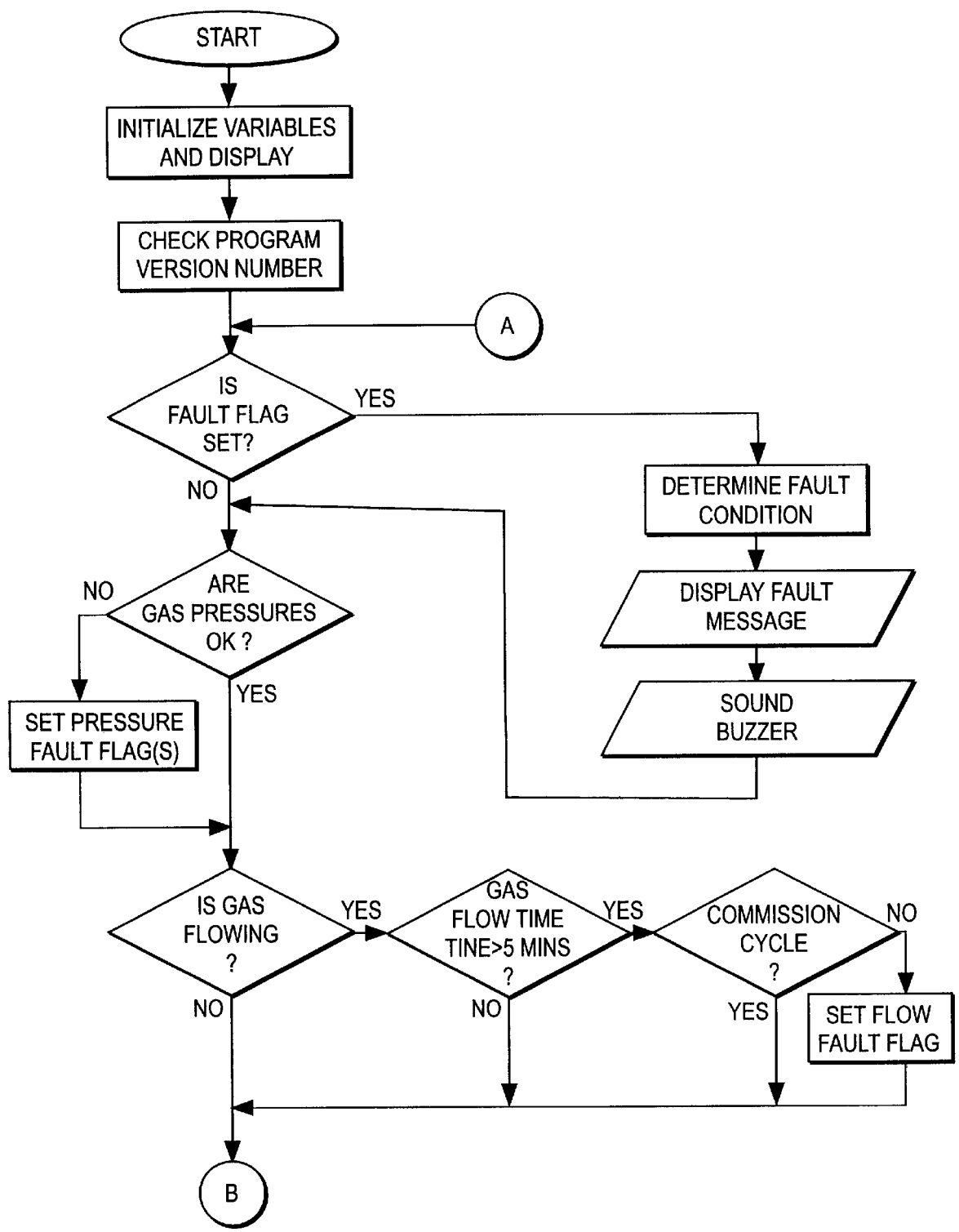

FIGS. 5A, B, C show flow diagram(s) for the show embodiment of FIG. 4.

Figure 3:
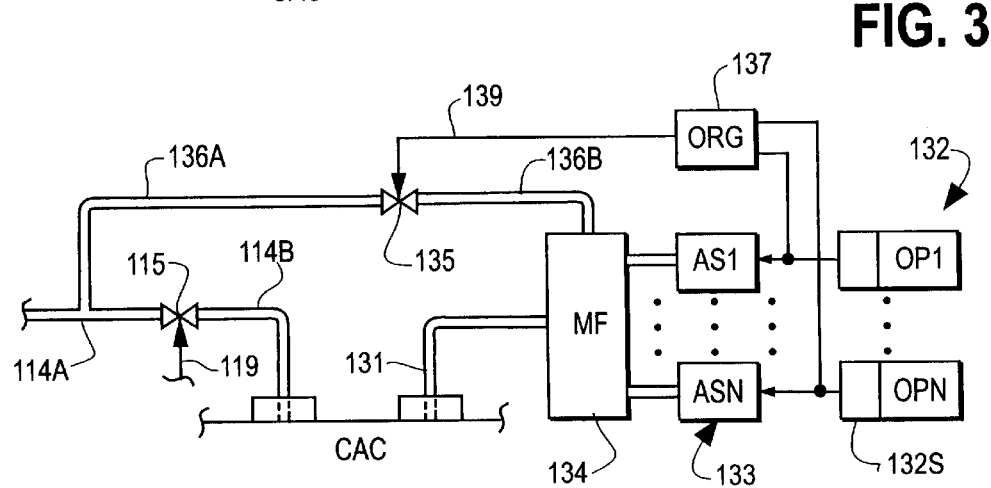
Figure 5B:
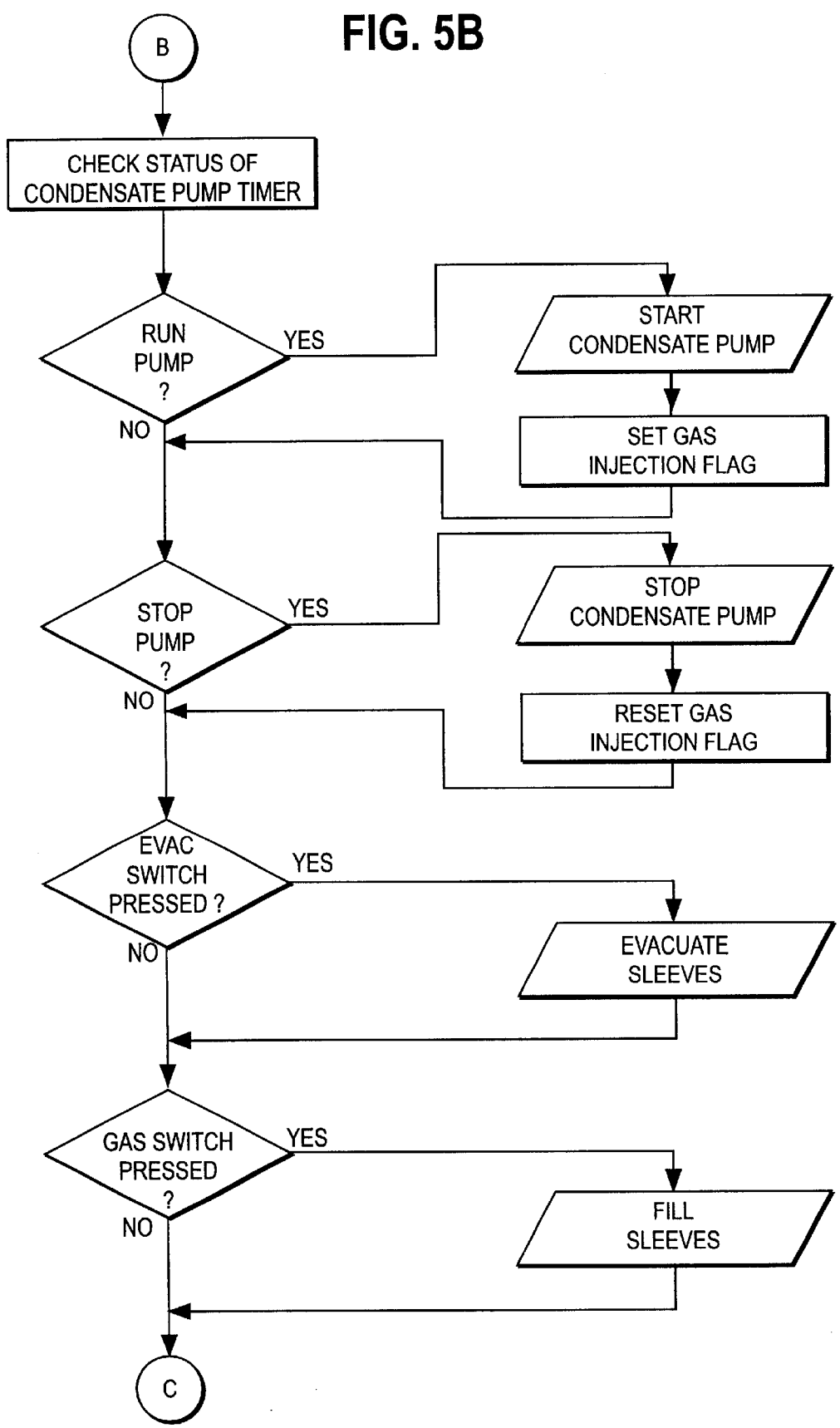
Figure 5C:
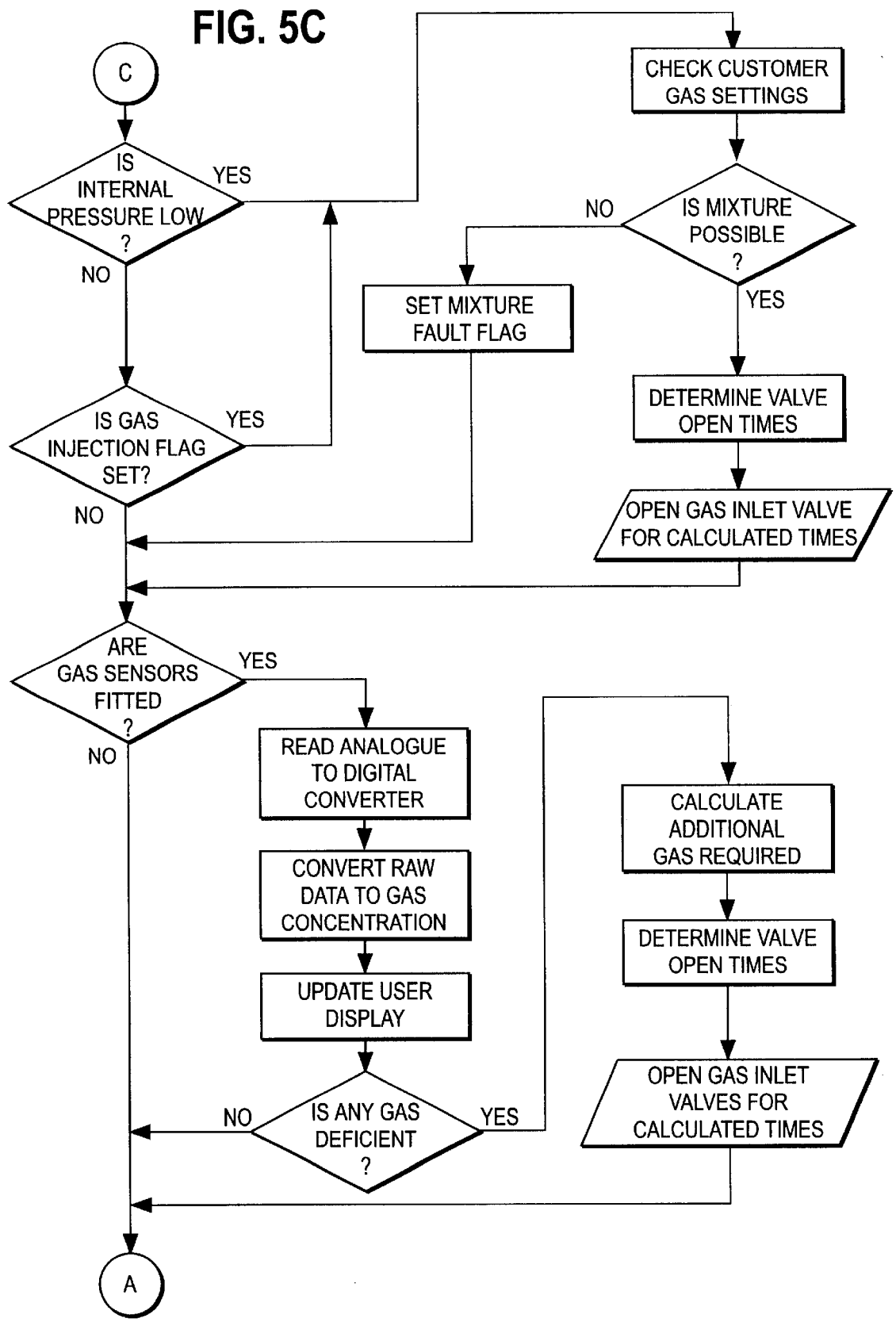

The embodiment and modifications/alternatives of FIGS. 1–3 were first developed as add-on provisions for anaerobic cabinets found to experience unexpected loss of adequate anaerobic internal atmosphere conditions; and afforded an immediate solution irrespective of reasons for such loss, as well as having wider application to other controlled atmosphere cabinets and immediately appreciated scope for further development and refinement eventually resulting in the embodiment of FIGS. 4 and 5.

In FIG. 1, a controlled atmospheres cabinet 110, specifically an anaerobic cabinet with user access porting 111A, 111B through its transparent front 110F and entry lock provision 112 (which could be internal and/or associated with the porting 111A, B), is shown supplied with a pressurised gas mixture from a regulated cylinder 113 over conduits or pipes 114A, 114B through conventional relay- and/or solenoid-operated valve 115. A separate entry lock provision 112 as shown may well have atmosphere flushing etc, whether from the main chamber of the cabinet 110 for branched from supply 113, 114 and separately controlled. In use, the valve 115 is opened whenever and whilst internal cabinet atmosphere pressure falls and remains below some predetermined level, usually a small over-pressure compared with external ambient pressure, causing a pressure switch 116 to open the valve 115, see electrical connection from its terminal 117A connected to line 119.

The valve opening line 119 is also shown fed from output of a timer 121, which may be variable, see dashed for setting provision 121S. The timer 121 is preferably settable both as to interval between energisations of its output and as to durations of such output energisations, whether by service, etc engineers' settings or by operator setting, see line 121T, including through such as analogue potentiometer etc type knob(s) or slider(a) etc or such as numeric keyboard operation.

Usually, in order to ensure that an anaerobic cabinet not to go aerobic,, perhaps due to greater that expected rates or times of loading/unloading when act up for maximum economy and/or using gas mixtures of below 10% hydrogen content, it is has been established as normally sufficient to have only a few seconds of timer-controlled duration of atmosphere enhancement each hour or so, though that is a matter for variation as required or preferred, including greater or lesser durations at longer or shorter intervals. The timer 121 is shown interlocked with complementary output 112B from tie pressure switch 116, whether at each or selected operations of the pressure switch 116, simply to assure independence of respective valve opening control, perhaps temporarily to disable or to interrupt incrementing of a timer counter or to reset its interval timing; or to ensure enhancement immediately or otherwise predeterminedly after each loading/unloading usage of the cabinet, say by forcing a counter state; and/or temporarily to select alternative duration for opening the valve 115; or whatever condition may be found to be helpful in terms of timer control.

FIG. 1 further bas dashed indication of other provision(s) 122 for operating the timer 121 according to some other parameter, including as an on-demand operation of its output for its set or some selected duration, see line 123. Alternatively, another and independent timer, or different duration setting provision 124, may be made feeding directly to the valve operating line 119. Such other parameter may be of atmosphere or other conditions inside the cabinet 110, or of usage rate/durations of entry lock provisions, or of environmental conditions such as ambient humidity outside the cabinet 110, all as can be detected automatically by suitable sensors or control system monitoring; or of samples being cultured, as may be pre-set but requiring entry via selection to provisions of the cabinet control system. There can, of course, be as many other parameter provisions 122 as required or desired, and some may be of efficiently combined and/or multiplexed regarding timing etc, say using programmed microprocessor control.

FIG. 2 shows a modification or alternative where an additional supply 125, say of hydrogen (or some other additive appropriate to some other parameter), is activated by branch 126 from feed connection to line 119 and applied to the normal atmosphere maintaining gas(es) through an appropriate mixing provision 127, whether of passive, nature, or active and requiring actuation (see further dashed branch from line 119).

Such additional component supply could, of course, be directly to the cabinet 110, as at 131 in FIG. 3, which shows at 132 plural other parameter-dependent operating provisions OP1–OFN each with its own duration setting stage 132S (though some could share same if appropriate), for operation of its own additional component supply means 133 through a delivery manifold 134. It will be appreciated that programmed microprocessor control will be of useful simplifying effect as interface input, between sensors and output signals each readily timed as to their occurrence and durations. Further provision is shown for other or standard atmosphere gas(es) to scour the delivery manifold and/or appropriately dilute the added component, by way of opening valve 135 in a branch line 136 from the basic atmosphere gas supply 114A, as may be useful for at least some of the added components for which outputs are shown taken through OR-gate 137 to valve control line 139.

It will be appreciated that such provisions 131–139 may be extra provisions compared with basic and/or more sophisticated operation by way of extra pulses of pressurised atmospheric gas alone.

Turning to FIG. 4, prescribable atmosphere cabinet shown with gloved/sleeved manipulation access ports 211A, B through transparent front 210F; related individual gas supplies 212A–D and associated flow valves 213A–D; overall gas manifold 215 and supply isolation valve 216; control/instrument ate panel 220 in relation to a data display 221 and data entry keypad 222 (both further shown separately for convenience); and programmable logic controller 230 typically affording PROM program storage, digital data processing, configurable logic, and input and output provisions 231 and 232 additional to display output and data input bus provisions 233 and 234 associated with display 221 and keypad 222.

The cabinet 210 may provide access through lock provisions built into the ports 211A, B as we have lately been providing. However, other access lock provisions could be made, say, normally as at 112 in FIG. 1, or otherwise, say as we have also lately been providing.

Prescribing atmosphere for interior of the cabinet 210 is under operator control through keypad 222, but preferably code-word protected. One particular arrangement of keypad 222 and associated display 221 has keys or touch-pads for various generally conventional purposes, including data message display M, which may be considered/used as a normal display mode, say showing current prescribed atmosphere, which, in the illustrated case, will be as percentages of hydrogen (225B), oxygen (225C), carbon dioxide (225D) and nitrogen (225A), perhaps further indicating any departure (s) therefrom where the cabinet 210 has individual component gas sensor,(s), say for up to each of hydrogen, oxygen and carbon dioxide with nitrogen being treated as a computable balance. Use of the key/pad (A) for adjustment preferably will call for code/pass-word entry say as a decimal number using up to four or more digit positions using the plus (+) and minus (–) keys/pads for each digit position and the arrow keys for moving between digits, making such use as may be required of the clear (C) key/pad before using the entry (E) key/pad. Correct entry of the code/pass-word will give access for similar data entry relative to the desired change of prescribed atmosphere. A highly useful and advantageous feature is preferably built into the logic-controller 30, namely capability for disallowing certain atmosphere specifications, whether in view of established effectiveness criteria or for other reasons such as safety, e.g. for the gases shown in the drawing, not allowing more than predetermined maxima for hydrogen (say up to 9%) and/ or oxygen (say up to 20%) and/or carbon dioxide (say up to 20%), nor permitting an explosive, even flammable or flame supporting, mixture—say limited against known objectionable percentages of 5% or more hydrogen in 6% or more oxygen.

Two other keys/pads are shown, one (O) being an overall options menu, including to give access to such as making changes to the code/pass-word, and the other serving the well-known purpose of giving engineers' access to data concerning actual functioning and/or diagnostics for the cabinet 210.

Relative to any particular prescribed atmosphere, the programmable logic controller 230 will compute individual gas supply requirements, which, at simplest, may be as times for individual gas flows at nominal flow rates from compressed cylinders 212A–D therefor through preset types of valves 213A–D. However, it is further feasible and practicable for actual individual gas flow rates to be sensed and times computed accordingly. Alternatively, settings might be computed for application to output valve gear of the cylinders 212A–D and/or for application to variable flow-rate types of valves 213A–D, and for such settings to be applied automatically over suitable further connection provisions than are presently illustrated.

Other controller inputs 235 are shown including outputs from normal over-pressure and higher over-pressure sensors 236 and 237: actually being shown further additional to lines from the individual gas content sensors 225A–C. Specific venting valve 238 is also shown for the cabinet 210 along with preferably peristaltic type condensate removal pump 239, see as controlled by respective outputs 240 of the programmable logic controller 230 having other outputs to control individual gas supply valves 213A–D and overall isolating valve 216.

Operation matching what is already known can involve response to lower than normal slight over-pressure, sensed at 236, causing simple or computed operation of the valves 213A–D (if appropriate 216) for supply of gases according to prescribed proportions until or so that normal slight over-pressure is reached, perhaps usefully ensuring small excess to require operation of venting at 238. Additional operation to add periodic, i.e. regular, or on-demand, i.e. including according to some specific criteria, further amounts of gases is readily afforded by programming and/or operators' command and/or according to entered data at and by the controller 230. Such further gas supply operation can be simply in accordance with atmosphere as originally or nominally specified; or different as might be entered by an operator for corrective or other reasons; or according to information and/or computation relative to differential gas effects for actual or intended samples in or for the cabinet 210; or, indeed, as a direct response to individual gas content sensed at 225A–C requiring individual or other adjustment.

Operational options further include either not venting for additional gas supply resulting in between normal overpressure (236) and higher (but still safe) over-pressure (237), or perhaps venting less quickly than such supply will increase overpressure. Combination of positive additional gas supply and cabinet atmosphere removal or venting is seen a beneficial circulation at least better approaching nominal atmosphere specification. Convenience suggests simultaneous removal of accumulated condensate by at least partially synchronous operation of the peristaltic pump 239, which can, of course, itself contribute to circulation and atmosphere removal and replacement.

Operator usage, particularly loading and unloading, and amount of microbial growth of particular loads, will obviously affect need for additional supply of gas(es), and relevant data entered by the operator can facilitate useful calculation by the controller to set parameters including durations and intervals between such actions.

One practical flow diagram for program-controlled microprocessor-based, control logic and processing block 230 is given in FIG. 5 relative to decision-making (diamond), function-performing (parallelogram) and various flag-setting (rectangle) steps well-known for computer programs, and all of which are believed to be self-explanatory in the light of preceding description.

What is claimed is:

1. Controlled atmosphere cabinet for microbiological work in which samples can be tested and manipulated, the cabinet comprising an enclosure with means providing all of visibility of its interior from outside, a gas supply for providing a desired or target composition of internal atmosphere, means for controlled lock-type access for manual introduction and removal of items, hand/arm access port provision for manipulation of said samples in the cabinet; first control means for sensing a first internal pressure in said cabinet and operative during use of the cabinet for said gas supply of said desired or target composition to be relative to maintaining said first internal pressure in said cabinet, and further control means including means for sensing a second internal pressure of said cabinet higher than said first internal pressure and operative an additional gas supply to correct or compensate for effects actually or potentially adverse to maintaining said desired or target composition of the internal atmosphere.

2. Controlled atmosphere cabinet according to claim 1, comprising operator-actuated input means to which the further control means is responsive for said additional gas supply.

3. Controlled atmosphere cabinet according to claim 2, wherein the operator-actuated input means includes selection of sample and/or cabinet usage-related parameters to select prescribed regimes(s) of operation of the further control means for said additional gas supply.

4. Controlled atmosphere cabinet according to claim 1, further comprising means for sensing prescribed conditions to which the further control means is responsive for said additional gas supply.

5. Controlled atmosphere cabinet according to claim 4, further comprising means for sensing particular content(s) of one or more of constituent gases of said desired or target compensation.

6. Controlled atmosphere cabinet according to claim 1, further comprising selectively operable venting means for venting the internal atmosphere, wherein the further control means is operative for, said additional gas supply in conjunction with selecting operation of the venting means.

7. Controlled atmosphere cabinet according to claim 1, wherein the further control means is operative for said additional gas supply by way of adding gas in said desired or target composition.

8. Controlled atmosphere cabinet according to claim 1, further comprising individual gas supply controlling means for selectively controlling supply of one or more constituent gases of said desired or target composition, wherein the further control means is operative for said additional gas supply in conjunction with the individual gas supply controlling means to add at least one gas as may be appropriate for desired correction or compensation.

9. Controlled atmosphere cabinet according to claim 8, wherein the further control means is operative for said additional gas supply by selecting duration(s) of flow requirement by the individual gas supply controlling means.

10. Controlled atmosphere cabinet according to claim 8, wherein the further control means is operative for said additional gas supply by selecting rate(s) of flow requirement by the individual gas supply controlling means.

11. Controlled atmosphere cabinet according to claim 1, further comprising selectively operable condensate removal means for positive removal of any condensate accumulated in the cabinet, wherein the further control means is operative to select operation of the condensate removal means in conjunction with said additional gas supply.

12. Method of operating a controlled atmosphere cabinet for microbiological work in which samples can be tested and manipulated, comprising steps of:

providing a cabinet with an interior visible from outside;

providing a controlled lock-type access for manual introduction and removal of items and hand/arm access port provision for manipulation of said samples in the cabinet;

providing a controlled gas supply of desired or target composition for maintaining an internal cabinet atmosphere;

maintaining a first internal pressure in the cabinet by controlling said desired or target composition of the gas supply during use of the cabinet; and providing correction or compensation for effects actually or potentially adverse to maintaining said internal atmosphere by said gas supply of desired or target composition by further controlling an additional gas supply relative to a second internal pressure of said cabinet, said second internal pressure being higher than said first internal pressure.

13. Method according to claim 12, wherein said additional gas supply is of like composition to said desired or target composition.

14. Method according to claim 12, wherein said additional gas supply is of different composition to said desired or target composition.

* * * * *